United States Patent [19]

Walker

[11] Patent Number: 4,489,087
[45] Date of Patent: Dec. 18, 1984

[54] SPERMICIDAL THIOKETAL SUBSTITUTED N-ALKYL IMIDAZOLES

[75] Inventor: Keith A. M. Walker, Los Altos Hills, Calif.

[73] Assignee: Syntex (U.S.A.) Inc., Palo Alto, Calif.

[21] Appl. No.: 434,088

[22] Filed: Oct. 13, 1982

[51] Int. Cl.³ .................. A61K 31/415; C07D 409/06
[52] U.S. Cl. .............................. 424/273 R; 548/336; 548/341
[58] Field of Search ............................. 548/336, 341; 424/273 R

[56] References Cited

U.S. PATENT DOCUMENTS 4,277,486  7/1981  Walker ............................. 548/336 X

FOREIGN PATENT DOCUMENTS 2342728  9/1977  France ............................. 548/341

*Primary Examiner*—Richard A. Schwartz
*Attorney, Agent, or Firm*—James M. Kanagy; Tom M. Moran

[57] ABSTRACT

Compounds of the formula:

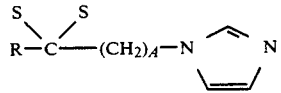

(I)

wherein

R is alkyl of 1 to 12 carbon atoms, cyclopentyl, cyclohexyl, cyclopentylloweralkyl or cyclohexylloweralkyl;

Z is ethylene or propylene, optionally substituted with a single substituent which is lower alkyl;

A is the integer 1, 2, or 3; and the pharmaceutically acceptable acid addition salts thereof, said compounds being useful as spermicidal, antimicrobial and anticonvulsant agents and thromboxane synthetase inhibitors.

19 Claims, No Drawings

4,489,087

SPERMICIDAL THIOKETAL SUBSTITUTED N-ALKYL IMIDAZOLES

BACKGROUND OF THE INVENTION

1. Field of the Invention

This invention relates to certain N-alkyl imidazoles substituted on the alkyl chain by a cyclic thioketal moiety. These compounds are spermicidal and therefore useful as contraceptive agents in male and female mammals. The invention also relates to the use of these compounds as spermicidal and antimicrobial agents and for the prevention and/or treatment of convulsions in mammals. In addition they have utility as thromboxane synthetase inhibitors. This invention also relates to a process for preparing these compounds, to compositions thereof, and to methods of use.

2. Related Disclosure

There are several publications that disclose imidazole compounds which have spermicidal, antimicrobial and anticonvulsant activity. The most pertinent are U.S. Pat. Nos. 4,150,153; 4,101,666; 4,101,665; 4,101,664; 4,078,071; 3,578,999; 3,793,453; German Pat. No. 2,602,770; and British Pat. No. 837,997. Imidazole ketals having spermicidal activity are disclosed in U.S. Pat. No. 4,247,552. There are also two articles which should be noted. One is by Dixon, D. W. et al, *Chem. Therapy* (Basel) 24 (6), 365–7, 1978 and the second by Godefroi, E. F. et al, *J. Med. Chem.* 12 (5), 784–91, 1969.

SUMMARY OF THE INVENTION

A first aspect of the invention is the compounds represented by the formula

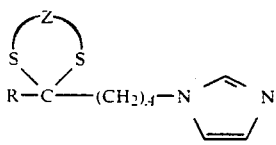 (I)

wherein
R is alkyl of 1 to 12 carbon atoms, cyclopentyl, cyclohexyl, cyclopentylloweralkyl or cyclohexylloweralkyl;
Z is ethylene or propylene, optionally substituted with a single substituent which is lower alkyl;
A is the integer 1, 2, or 3; and
the pharmaceutically acceptable acid addition salts thereof.

A second aspect of the present invention is a method for combatting and controlling fungi, bacteria and protozoa by administering one or more compounds of Formula (I), either alone or in admixture with a vehicle or excipient to an infected subject or one susceptible to infection.

Another aspect of this invention is a method for preventing or controlling convulsions in mammals by administering one or more compounds of Formula (I) alone or in a composition.

A further aspect of the present invention is a method for effecting contraception which consists of administering a compound of Formula (I) or a composition containing same to a male or female mammal.

An additional aspect is a method for inhibiting thromboxane synthetase in a mammal which method comprises administering an effective amount of one or more of the subject compounds to a mammal, either alone or in combination with a pharmaceutically acceptable carrier.

Further, this invention relates to pharmaceutical compositions containing one or more of the compounds of Formula (I) formulated in at least one suitable solid or liquid excipient which can be administered by numerous routes or techniques, whichever may be most appropriate to the situation at hand.

Also included in this invention is a process for preparing the compounds of Formula (I) wherein a compound of the formula

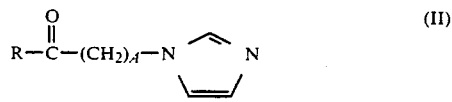 (II)

is treated with a 1,2 or 1,3-dithiol to form a cyclic thioketal of Formula (I).

The bases of this invention may be readily converted to their acid addition salts by treating the free base of a compound according to Formula (I) with at least an equivalent of a selected inorganic or organic acid. Acid addition salts are converted to the free base by treatment of the acid addition salt with an equivalent of inorganic or organic base. In another instance, one acid addition salt may be converted to a second acid addition salt by treatment of one salt with at least at least an equivalent of a second inorganic or organic acid.

The compounds, compositions and methods for making the various aspects of the present invention noted above will become more readily apparent from the description following.

DESCRIPTION AND PREFERRED EMBODIMENTS

Various terms used herein should be understood to read according to the following annotations unless otherwise specified.

The term "alkyl of 1 to 12 carbon atoms" refers to a straight or branched chain monovalent substituent consisting solely of carbon and hydrogen with no unsaturation and containing from 1 to 12 carbon atoms. Examples of such alkyl groups are methyl, ethyl, n-propyl, i-propyl, n-butyl, sec-butyl, t-butyl, n-pentyl, n-hexyl, n-heptyl, n-octyl, n-nonyl, n-decyl, n-undecyl, n-dodecyl and the various branched alkyl isomers of the mentioned n-alkyl compounds. "Lower alkyl" means straight chain alkyl compounds as defined above but limited to 1 to 4 carbon atoms. In the absence of a specific designation such as t to denote the tertiary form, all alkyl groups recited herein are the normal or straight chain moiety. "Cyclopentylloweralkyl" means that the cyclopentyl moiety is attached to the 2 position carbon of the thioketal ring by means of a 1 to 4 carbon chain as per the definition of lower alkyl in the preceeding paragraph. "Cyclohexylloweralkyl" refers to the same substituent except that cyclohexane is the terminal moiety rather than cyclopentane.

The phrase "pharmaceutically acceptable acid addition salts" denotes salts of the free base which possesses the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid or phosphoric acid. Examples of organic acids are acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid, and the like.

Compounds of Formula (I) wherein Z is substituted ethylene or propylene exist as geometric (i.e. cis and trans) isomers relative to the thioketal ring. Both isomers and mixtures thereof are to be included in the scope of this invention. Any discussion of synthetic routes should be understood to include, where appropriate, both geometric isomers unless specifically stated otherwise. if desired, the respective geometric isomers of compounds of Formula (I) may be separated by methods well known in the art. Such methods may include, for example, chromatography, fractional crystallization, high-pressure liquid chromatography, and the like.

Furthermore a chiral center is present at the 4-position of the thioketal ring when a substituent is there present. Therefore, synthesis may produce an optical isomer or a racemic mixture. The scope of this invention covers both forms, but unless otherwise noted the racemic mixture will be present.

Racemic mixtures of compounds according to Formula (I) may be resolved into the respective optical isomers by known conventional methodology. Such procedures would involve the reaction of a racemic mixture with an optically active acid and fractional crystallization of the resultant salt or by the use of some other appropriate method for separating optically active salts.

The compounds of Formula (I) may be considered to consist of two subclasses, those of Formulas (Ia) and (Ib), shown below:

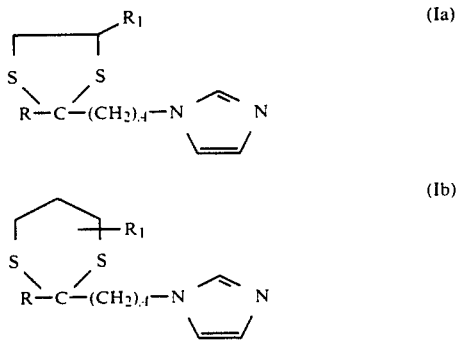

wherein R₁ is hydrogen or a lower alkyl group and R and A are as defined above.

One preferred subgenus of compounds of Formulas (Ia) and (Ib) is that wherein A is 1 or 2 and R is straight chain alkyl and R₁ is hydrogen. The more preferred group of compounds is that wherein A is 1 or 2 and R is alkyl of 4 to 10 carbon atoms.

The most preferred compounds of Formula (I) are those wherein A is 1 and R is 6 to 10 carbon atoms or A is 2 and R is 5 to 9 carbon atoms; and the pharmaceutically acceptable acid addition salts thereof.

Most preferred compounds of Formula (I) are:
1-[[2-(hexyl)-1,3-dithiolan-2-yl]methyl]imidazole hydrochloride, m.p. 131°–135° C.;
1-[[2-(heptyl)-1,3-dithiolan-2-yl]methyl]imidazole;
1-[[2-(octyl)-1,3-dithiolan-2-yl]methyl]imidazole hydrochloride, m.p. 136°–138° C.;
1-[[2-(heptyl)-1,3-dithiolan-2-yl]ethyl]imidazole hydrochloride, m.p. 110°–116° C.;
1-[[2-(octyl)-1,3-dithiolan-2-yl]ethyl]imidazole; and
1-[[2-(nonyl)-1,3-dithiolan-2-yl]ethyl]imidazole,
and the pharmaceutically acceptable acid addition salts thereof.

UTILITY AND ADMINISTRATION

The compounds of Formula (I) herein and the pharmaceutically acceptable non-toxic acid addition salts thereof are useful as spermicides, either intravaginally administered to the female mammal or orally or parenterally administered to the male mammal.

"Spermicide" and "spermicidal" refer to the capacity to render spermatozoa ineffective. This effect may be the result of actual sperm cell death, or less drastically, immobility, cell membrane alteration or other impairment which results in the inability of the sperm cell to effect fertilization.

Compositions appropriate for such uses are prepared by methods and contain ingredients which are well known in the art. A generally recognized compendium of such methods and ingredients is *Remington's Pharmaceutical Sciences* by E. W. Martin, (Mack Publ. Co., 16th Ed., 1980).

For intravaginal administration suitable formulations are, for example, creams, gels, spray foams, suppositories and the like, as well as slow release materials. Each composition contains an effective amount of active ingredient plus one or more pharmaceutically acceptable excipients. Such excipients are, for example, starch, glucose, lactose, talc, cellulose and the like for solid formulations; polyethylene glycols, modified vegetable oils, mineral oil, or polyalkylene glycols and the like for semi-solid formulations; and water, alcohols, glycerol, lanolin, mineral oil and the like for liquid or semi-liquid compositions. The compositions may contain between about 0.01 and 10.0 percent by weight of the active ingredient, preferably between 0.1 and 1.0%, and may, if desired, contain other active ingredients. Such compositions may also be used in conjunction with barrier methods such as, e.g., diaphragms or condoms.

In the practice of the method of contraception herein, the above formulations are administered to the female before coitus, within a period of about 12 hours prior thereto. The preferred dosage range of active ingredient is from about 1 mg to 20 mg per vaginal administration for an adult human. For smaller mammals the amount would be correspondingly smaller.

Compositions for administration to the male are preferably directed to oral administration, although parenteral administration is also biologically possible. Such compositions will contain a spermicidal amount of active ingredient with a non-toxic, pharmaceutically effective carrier. For said oral administration solid dosage forms such as tablets, capsules and powders may contain such excipients as, for example, lactose, starch, or cellulose.

In the practice of the method of contraception herein, a dose in the range of between about 0.1 and 10 mg active ingredient per kg will be administered to the male prior to coitus, preferably at least 1 hour before coitus, and more preferably daily for 3–7 days prior to coitus.

The above described compounds of Formula (I) also exhibit antifungal, antibacterial and antiprotozoal activity. For example, compounds of the present invention exhibit antifungal activity against human and animal pathogens such as
*Microsporum audouini,*
*Microsporum gypseum,*
*Microsporum gypseum—canis,*
*Epidermophyton floccosum,*
*Trichophyton mentagrophytes,*
*Trichophyton rubrum,*
*Trichophyton tonsurans,*
*Candida albicans,* and
*Cryptococcus neoformans.*

The compounds of the present invention also exhibit antifungal activity against the following fungi primarily of agricultural significance
*Aspergillus flavus,*
*Cladosporium herbarum,*
*Fusarium graminearum,*
*Penicillium notatum,*
*Aspergillus niger,*
*Penicillium oxalicum,*
*Penicillium spinulosum,* and
*Pithomyces chartarum.*

In addition, the compounds of the present invention exhibit antibacterial activity against human and animal pathogens, such as
*Staphylococcus aureus,*
*Streptococcus faecalis,*
*Corynebacterium acnes,*
*Erysipelothrix insidiosa,*
*Escherichia coli,*
*Proteus vulgaris,*
*Salmonella choleraesuis,*
*Pasteurella multocida,* and
*Pseudomonas aeruginosa.*

Moreover, the compounds of the present invention exhibit antiprotozoal activity against protozoa such as *Trichomonas vaginalis.*

A further aspect of this invention relates to a composition for pharmaceutical, agricultural and industrial antimicrobial use. This composition includes an effective amount of one of the disclosed compounds and a suitable carrier. Still further is the application of this composition to a subject infected with or susceptible to attack by fungi, bacteria or protozoa. The application is in the amount necessary to prevent infection or arrest further growth whether in an composition or alone. Compositions of these compounds may be formulated as solids, semi-solids or in a liquid form. Tablets, capsules, powders, creams, suppositories, lotions, ointments, sprays and such may be used as formulations. Pharmaceutically acceptable non-toxic carriers or excipients normally employed for solid formulations include tricalcium phosphate, calcium carbonate, kaolin, bentonite, talc, gelatin, lactose, starch and the like; for semi-solid formulations there may be mentioned, for example, polyalkylene glycols, vasoline and other cream bases. For liquid formulations there may mentioned, for example, water, oils of vegetable origin and low boiling solvents such as isopropanol, hydrogenated naphthalenes and the like. Compositions containing these compounds may also include preservatives, stabilizing agents, emulsifying agents, salts for the adjustment of osmotic pressure and buffers. Other therapeutic agents may also be included in the composition.

In pharmaceutical applications, the subject compounds and compositions may be administered to humans and animals by conventional methods such as topically, orally, or parenterally. Parenteral administration includes intramuscular as well as subcutaneous and intraveneous administration. Topical application is the preferred method of administration for antimicrobial application. An area affected by fungal, bacterial or protozoal growth or an area that is subject to infection by one of these microbes may be treated with subject compounds or compositions by dusting, sprinkling, spraying, rinsing, brushing, dipping, smearing, coating, impregnating and the like. The weight of compound contained in these compositions may vary anywhere from 0.1 to 10% by weight of the composition, a quantity sufficient to inhibit or prevent microbial growth.

Pharmaceutical compositions typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g., oral or parenteral) administration, it is expedient to administer the active ingredient in amounts between about 1 and 100 mg./kg. body weight per day, preferably between about 5 and 50 mg./kg. body weight per day, preferably distributed over several applications (e.g., in 3 individual doses) in order to achieve the most effective results. For localized (e.g. topical) administration, however, proportionately less of the active ingredient is required.

The subject compounds, being also useful in agricultural applications may be applied directly to plants, seeds, and the soil. Seeds may be treated by a powdered carrier by mixture with a conventional surface active wetting agent with or without additional solid carrier. Examples of powdered carriers are the various mineral silicates such as mica, talc, pyrophylite and clays. Any known surfactant such as an ionic, non-ionic amphoteric or cationic type may be used. Treatment of plants with a subject compound may be carried out by means of an aqueous spray in combination with the surface active agent, a hydrocarbon solvent, or a powdered solid carrier. One or more subject compounds in admixture with the mentioned carriers will generally be applied to the foliage of the plant. Control of fungi and the like in soil by the subject compound may be carried out by applying said compounds as a dust in admixture with the sand, soil or a powdered solid carrier such as a mineral silicate with or without additional surface acting agents. In this instance the subject compounds can also be applied by aqueous spray to the soil, wherein the spray may or may not contain a surfactant and a powdered solid carrier.

Subject compounds of this disclosure may also be used in industrial settings. Of particular importance in this instance is their use as preservatives in food to prevent and combat microbial growth which can cause deterioration and spoilage. In this or any of the above-mentioned applications the subject compounds may be used alone or in conjunction with other pesticidal controlling agents such as fungicides, bactericides, insecticides, miticides and the like.

Another aspect of the present invention relates to a method for treating and/or preventing convulsions in a mammalian subject comprising administering a therapeutically effective amount of the compound of Formula (I) or a pharmaceutically acceptable acid addition salt thereof.

Compounds of Formula (I) exhibit CNS related activity, in particular anticonvulsant activity. Initial anticonvulsant activity is determined using the maximal electroshock seizure test (*J. Pharmacol. Exp. Ther.* 96: 99–113, 1949) or modifications thereof.

Compounds of Formula (I) are also selective inhibitors of thromboxane synthetase and as such are useful for the treatment of vasospasms, blood platelet hyderaggregablity and thromboembolism associated with many cardiovascular diseases in man.

In the practice of the above described methods of the present invention, a therapeutically effective amount of the compound of Formula (I) or a pharmaceutical composition containing same is administered via any of the usual and acceptable methods known in the arts, either singly or in combination with another compound or compounds of the present invention, where there are pharmaceutical agents or other pharmaceutical agents. These compounds or compositions can thus be administered orally, systemically (i.e. intranasally or by suppository) or parenterally (i.e. intramuscularly, subcutaneously and intravenously), and can be formulated into solid or liquid dosages including tablets, solutions, suspensions and the like in the same manner as discussed hereinabove under the recitation regarding spermacidal and antimicrobial uses. Oral administration is preferred for the treatment of convulsions and cardiovascular disorders.

In view of the foregoing as well as in consideration of the degree of severity of the condition being treated, age of the subject and so forth, all of which factors are determinable by routine experimentation by one skilled in the art, the effective dosage in accordance herewith can vary over a wide range. Generally, a therapeutically effective amount for anti-convulsant use ranges from about 0.1 to about 300 mg/kg/body weight per day and preferably from about 0.3 to about 100 mg/kg body weight per day. In alternative terms, for an average adult human subject of about 70 kg, a therapeutically effective amount in accordance herewith would be, in preferred embodiments, from about 20 mg to about 7 g per day per subject.

PREPARATIONS

Compounds of Formula (I) may be prepared by various synthetic routes but as disclosed herein the preferred method is to form the N-alkyl imidazole of Formula II having a ketone group on the carbon backbone and then making the cyclic thioketal therefrom.

The compounds of Formula (I) may be prepared from a suitable ketone represented by Formula II as depicted in Reaction Scheme A wherein A is defined above and X is a leaving group, such as halo (chloro, bromo) or a sulfonate ester.

REACTION SCHEME A

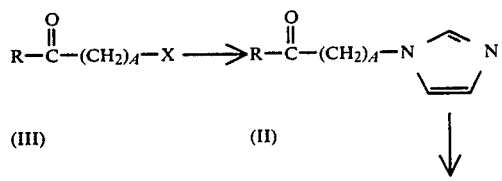

-continued

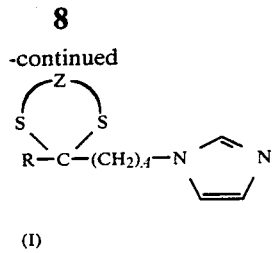

(A) The halo ketones of Formula III are generally known or are readily prepared using the methods disclosed in U.S. Pat. No. 4,078,071. The halo ketones wherein A is 1 are also conveniently prepared by oxidizing the corresponding halo alcohols, e.g. with Jones reagent. The halo alcohols are prepared by the method described in *J. Med. Chem.* 1978, 21, 840, and *J. Amer. Chem. Soc.* 1930, 52, 1164.

The haloketones wherein A is 1 are also readily prepared by, for example, conversion of of the acid chloride RCOCl to the diazoketone RCOCHN₂ with diazomethane, followed by treatment with acid HX.

(B) The imidazole ketones of Formula II are prepared according to the methods disclosed in U.S. Pat. No. 4,078,071, in particular by the methods disclosed in Reaction Schemes B, C, D, E, F and H, incorporated by reference herein. An additional useful method of making the final ketone precursors for the Reaction Scheme C in U.S. Pat. No. 4,078,071 consists of oxidation of a terminal olefin using selenium dioxide with or without added t-butyl hydroperoxide (*J. Amer. Chem. Soc.* 1977, 99, 5526) followed by oxidation of the resulting vinyl alcohol.

Compounds of Formula II may also be prepared by oxidizing the alcohols of Formula IV

REACTION SEQUENCE B

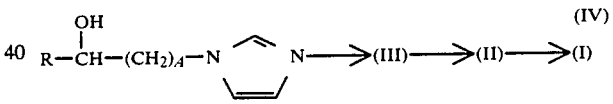

wherein R and A are as defined above by the method described in *J. Org. Chem.* 1979, 44 (23), 4148. Dimethyl sulfoxide is reacted with oxalyl chloride at −100° to −60° C. The intermediate formed is reacted with the alcohol of Formula IV to form an alkoxy sulfonium salt which is converted to the ketone of Formula II upon addition of triethylamine.

(C) The compounds of Formula II are converted to the compounds of Formula I by forming the cyclic thioketal as the last reaction step. This reaction may be carried out by a number of methods well known in the art, for example, by treatment of the ketone with at least 1 mole, but preferably an excess, of a dithiol in the presence of an acid or Lewis acid, for example, hydrogen chloride, zinc chloride, boron trifluoride or p-toluene sulfonic acid, with or without removal of water. A particularly useful method involves dissolving the imidazole-ketone and the appropriate dithiol in methanesulfonic acid as solvent. This reaction uses an equivalent amount or a molar excess, relative to the imidazole-ketone, of a 1,2- or 1,3-dithiol, and is carried out at ambient temperature or thereabouts for a time of 5 minutes to 24 hours, usually overnight.

The appropriate 1,2- and 1,3-dithiols are either available or readily accessible by known methods. Thus 1,2-dithiols may be obtained from episulfides (e.g. *Tetrahedron Letters*, 1973, 1401-4) or by the reduction of cyclic trithiocarbonates (e.g. *J. Chemical Society*, 1960, 1030-1036). The latter are prepared from episulfides, which themselves may be prepared by a variety of methods known in the art, e.g. from epoxides. Similarly, 1,3-dithiols are also available from cyclic trithiocarbonates, or from 1,3-diols, halides, or sulfonates by standard thiol-forming reactions.

The subject compounds of the instant invention can be isolated as free bases; however, since many of the compounds in base forms are oils, it is often more convenient to isolate and further characterize the compounds as acid addition salts. These salts are prepared in the usual manner, i.e. by reaction of the compound with a suitable inorganic or organic acid, described above. If desired, the salts can be readily converted to the compounds in base form by treatment with a base, such as potassium or sodium carbonate, or potassium or sodium hydroxide.

The following specific Preparations and Examples are illustrative of the present invention and should not be considered as limitative thereof in any manner.

PREPARATION 1

This preparation illustrates the conversion of imidazole-hydroxy compounds according to Formula IV to the imidazole-ketone compounds of Formula II by Reaction Sequence B. The compounds of Formula V are readily available or may be prepared by methods set out in U.S. Pat. No. 4,078,071 as noted herein above.

Oxalyl chloride (3.0 ml) in methylene chloride (75 ml) was placed in a flask and cooled to $-50°$ C. to $-60°$ C. Dimethyl sulfoxide (5.1 ml) in 15 ml of methylene chloride was then added followed by 5.88 g of 1-(3-hydroxyoctyl)imidazole dissolved in 30 ml of methylene chloride. The reaction mixture was stirred for 30 minutes at the initial temperature. Triethylamine (21 ml) was added to the reaction mixture which was then allowed to warm to room temperature. Water (100 ml) was added, the organic layer separated and the aqueous layer extracted with methylene chloride (2×50 ml). The organic layers were dried over MgSO$_4$ and the solvent removed to give 1-(octan-3-on-1-yl)imidazole as an oil.

Similarly, proceeding as above, but substituting the appropriate alcohol for 1-(2-hydroxybutyl)imidazole there may be prepared, for example, the following compounds of Formula (II):
1-(propan-2-on-1-yl)imidazole;
1-(pentan-2-on-1-yl)imidazole;
1-(undecan-2-on-1-yl)imidazole;
1-((6-cyclohexane)hexan-2-on-1-yl)imidazole;
1-(tetradecan-2-on-1-yl)imidazole;
1-(heptan-3-on-1-yl)imidazole;
1-(nonan-3-on-1-yl)imidazole;
1-(decan-3-on-1-yl)imidazole;
1-(dodecan-3-on-1-yl)imidazole;
1-(tetradecan-3-on-1-yl)imidazole;
1-(undecan-4-on-1-yl)imidazole;
1-((7-cyclopentane)heptan-4-on-1-yl)imidazole;
1-(dodecan-4-on-1-yl)imidazole;
1-(nonan-4-on-1-yl)imidazole;
1-(tridecan-4-on-1-yl)imidazole;

PREPARATION 2

This preparation illustrates the preparation of imidazole-ketones (Formula II) from the compounds of Formula III wherein A is 2 or less as set out in reaction Scheme A.

1-Chloro-2-hexanone (67.5 g) was added portionwise over half an hour to a stirred suspension of imidazole (175 g) in dimethylformamide (150 ml) at 0° C. and the mixture stirred overnight at ambient temperature. The resulting solution was poured into water (1500 ml), and the mixture extracted with ethyl acitate. The extracts were washed with water, dried (magnesium sulfate), evaporated, and the residue chromatographed on silica gel, eluting with 7% methanol in methylene chloride to give 1-(octan-2-on-1-yl)imidazole.

Similarly proceeding as above, but substituting the appropriate halo ketone for 1-chloro-2-butanone, there may be prepared, for example, the following compounds of Formula (II);
1-(hexan-2-on-1-yl)imidazole;
1-(heptan-2-on-1-yl)imidazole;
1-((2-cyclohexane)ethan-2-on-1-yl)imidazole;
1-(dodecan-2-on-1-yl)imidazole;
1-((4-cyclopentane)butan-2-on-1-yl)imidazole;
1-(decan-2-on-1-yl)imidazole;
1-(butan-3-on-1-yl)imidazole;
1-(pentan-3-on-1-yl)imidazole;
1-(hexan-3-on-1-yl)imidazole;
1-(cyclohexan-3-on-1-yl)imidazole;

PREPARATION 3

This preparation illustrates the preparation of imidazole-ketones (Formula II) from the compounds of Formula III wherein B is 3 as set out in reaction Scheme A.

1-Bromo-4-dodecanone 6.45 and imidazole (8.34 g) in dimethylformamide (10 ml) at 0° C. were stirred overnight at ambient temperature, then one day at 80° C. The resulting mixture was poured into water (200 ml), extracted with ether (3×75 ml) and the extracts were dried (magnesium sulfate) and evaporated. Chromatography of the product on silica gel eluting with 7% methanol in methylene chloride gave 1-(dodecan-4-on-1-yl)imidazole.

Similarly proceeding as above, but substituting the appropriate halo ketone for 1-chloro-4-dodecanone, there may be prepared, for example, the following compounds of Formula (II);
1-(butan-4-on-1-yl)imidazole;
1-(heptan-4-on-1-yl)imidazole; and
1-(decan-4-on-1-yl)imidazole.

PREPARATION 4

This preparation illustrates another method for preparing the imidazole-ketones of Formula II.

7.0 g of 2,4 dichlorobenzyl vinyl ketone (prepared by Jones oxidation of 2,4-dichlorobenzyl vinyl carbinol using the general method described in *J. Chem. Soc.*, 1966, 1972) in 350 ml of anhydrous ether was treated with 3.5 g of imidazole, the solution stirred overnight and then washed with water (3×30 ml). The solution was dried (MgSO$_4$) and evaporated to give 1-[4-(2,4-dichlorophenyl)propan-3-on-1-yl]imidazole. The hydrochloride salt was precipitated from ether and recrystallized from methanol/acetone, m.p. 105.5-110° C.

Alternatively 13.1 g of 2,4-dichlorobenzoylethyl-trimethylammonium iodide (prepared by Mannich reaction of 2,4-dichloroacetophenone with paraformaldehyde and trimethylamine hydrochloride, followed by quaternization with methyl iodide and ether) and 12 g of imidazole in dimethyl formamide (50 ml) were stirred overnight at room temperature and poured into 500 ml of water. The product was extracted with ether (3×300 ml), the extract washed with water (3×75 ml) and dried. Addition of ethereal hydrogen chloride precipitated the hydrochloride of 1-[3-(2,4-dichlorophenyl)-propan-3-on-1-yl]imidazole, which was recrystallized from methanol/acetone.

EXAMPLE I

This example illustrates the preparation of compounds according to Formula I(a) from Formula II type ketones.

A solution 1-(hexan-3-on-1-yl)imidazole (1.00 g) was stirred with ethane-1,2-dithiol (1 ml) at room temperature and then 1 ml of methanesulfonic acid was added in portions with cooling. After 15 minutes, 20 ml of methylene chloride was added and the mixture stirred for 4 hours. The reaction mixture was poured into 300 ml of methylene chloride which solution was washed with 3×100 ml 5% sodium hydroxide, 1×100 ml water and the organic layer dried over magnesium sulfate. Removal of the solvent afforded an oil which was chromatographed on silica gel, eluting with hexane, 50% hexane/ethyl acetate and ethyl acetate to yield 1.2 g of 1-[2-(2-propyl-1,3-dithiolan-2-yl)ethyl]imidazole. The residue was taken up in a small volume of ether and treated with ethereal hydrogen chloride until precipitation was complete. The resulting precipitate was filtered off and recrystallized from methanol/ethyl acetate, to give 1-[2-(propyl-1,3-dithiolan-2-yl)ethyl]imidazole hydrochloride, m.p. 118°–121° C.

Similarly proceeding as above, but substituting the appropriate ethane-1,2-dithiol and the appropriate ketone as exemplified in Preparations 1, 2 or 3 in place of 1-(hexan-3-on-1-yl)imidazole there may be prepared, for example, the following compounds:
1-[(2-methyl-1,3-dithiolan-2-yl)methyl]imidazole;
1-[(2-ethyl-1,3-dithiolan-2-yl)methyl]imidazole;
1-[(2-(4-cyclohexylbutyl)-1,3-dithiolan-2-yl)methyl]imidazole;
1-[(2-propyl-1,3-dithiolan-2-yl)methyl]imidazole;
1-[(2-cyclohexyl-1,3-dithiolan-2-yl)methyl]imidazole hydrochloride, m.p. 215°–223° C.;
1-[(2-n-butyl-1,3-dithiolan-2-yl)methyl]imidazole hydrochloride, m.p. 156°–159° C.;
1-[(2-pentyl-1,3-dithiolan-2-yl)methyl]imidazole;
1-[(2-butyl-1,3-dithiolan-2-yl)methyl]imidazole;
1-[(2-hexyl-1,3-dithiolan-2-yl)methyl]imidazole hydrochloride, m.p. 131°–135° C.;
1-[(2-heptyl-1,3-dithiolan-2-yl)methyl]imidazole;
1-[(2-cyclopentyl-1,3-dithiolan-2-yl)methyl]imidazole;
1-[(2-octyl-1,3-dithiolan-2-yl)methyl]imidazole hydrochloride, m.p. 136°–138° C.;
1-[82-nonyl-1,3-dithiolan-2-yl)methyl]imidazole;
1-[(2-(3-cyclopentylpropyl)-1,3-dithiolan-2-yl)methyl]imidazole;
1-[(2-decyl-1,3-dithiolan-2-yl)methyl]imidazole hydrochloride, m.p. 136°–137° C.;
1-[(2-undecyl-1,3-dithiolan-2-yl)methyl]imidazole;
1-[(2-dodecyl-1,3-dithiolan-2-yl)methyl]imidazole;
1-[(2-(2-cyclohexylethyl)-1,3-dithiolan-2-yl)methyl]imidazole;
1-[(2-ethyl-4-methyl-1,3-dithiolan-2-yl)methyl]imidazole;
1-[(2-methyl-4-methyl-1,3-dithiolan-2-yl)methyl]imidazole;
1-[(2-cyclohexyl-4-methyl-1,3-dithiolan-2-yl)methyl]imidazole;
1-[(2-n-butyl-4-methyl-1,3-dithiolan-2-yl)methyl]imidazole;
1-[(2-pentyl-4-methyl-1,3-dithiolan-2-yl)methyl]imidazole;
1-[(2-hexyl-4-methyl-1,3-dithiolan-2-yl)methyl]imidazole;
1-[(2-cyclopentyl-4-methyl-1,3-dithiolan-2-yl)methyl]imidazole;
1-[(2-nonyl-4-methyl-1,3-dithiolan-2-yl)methyl]imidazole;
1-[(2-decyl-4-methyl-1,3-dithiolan-2-yl)methyl]imidazole;
1-[(2-(4-cyclohexylbutyl)-4-methyl-1,3-dithiolan-2-yl)methyl]imidazole;
1-[(2-dodecyl-4-methyl-1,3-dithiolan-2-yl)methyl]imidazole;
1-[(2-ethyl-4-ethyl-1,3-dithiolan-2-yl)methyl]imidazole;
1-[(2-propyl-4-ethyl-1,3-dithiolan-2-yl)methyl]imidazole;
1-[(2-n-butyl-4-ethyl-1,3-dithiolan-2-yl)methyl]imidazole;
1-[(2-pentyl-4-ethyl-1,3-dithiolan-2-yl)methyl]imidazole;
1-[(2-hexyl-4-ethyl-1,3-dithiolan-2-yl)methyl]imidazole;
1-[(2-heptyl-4-ethyl-1,3-dithiolan-2-yl)methyl]imidazole;
1-[(2-nonyl-4-ethyl-1,3-dithiolan-2-yl)methyl]imidazole;
1-[(2-decyl-4-ethyl-1,3-dithiolan-2-yl)methyl]imidazole;
1-[(2-undecyl-4-ethyl-1,3-dithiolan-2-yl)methyl]imidazole;
1-[(2-dodecyl-4-ethyl-1,3-dithiolan-2-yl)methyl]imidazole;
1-[(2-ethyl-4-n-butyl-1,3-dithiolan-2-yl)methyl]imidazole;
1-[(2-methyl-4-n-butyl-1,3-dithiolan-2-yl)methyl]imidazole;
1-[(2-propyl-4-n-butyl-1,3-dithiolan-2-yl)methyl]imidazole;
1-[(2-cyclohexyl-4-n-butyl-1,3-dithiolan-2-yl)methyl]imidazole;
1-[(2-pentyl-4-n-butyl-1,3-dithiolan-2-yl)methyl]imidazole;
1-[(2-hexyl-4-n-butyl-1,3-dithiolan-2-yl)methyl]imidazole;
1-[(2-(2-cyclopentylethyl)-4-n-butyl-1,3-dithiolan-2-yl)methyl]imidazole;
1-[(2-decyl-4-n-butyl-1,3-dithiolan-2-yl)methyl]imidazole;
1-[(2-dodecyl-4-n-butyl-1,3-dithiolan-2-yl)methyl]imidazole;
1-[2-(2-methyl-1,3-dithiolan-2-yl)ethyl]imidazole hydrochloride, m.p. 156°–161° C.;
1-[2-[2-ethyl-1,3-dithiolan-2-yl)ethyl]imidazole;
1-[2-[2-propyl-1,3-dithiolan-2-yl]ethyl]imidazole hydrochloride, m.p. 118°–121° C.;
1-[2-[2-n-butyl-1,3-dithiolan-2-yl)ethyl]imidazole;
1-[2-[2-pentyl-1,3-dithiolan-2-yl)ethyl]imidazole hydrochloride, m.p. 105°–108° C.;
1-[2-[2-hexyl-1,3-dithiolan-2-yl)ethyl]imidazole;
1-[2-(2-heptyl-1,3-dithiolan-2-yl)ethyl]imidazole hydrochloride, m.p. 110°–116° C.;
1-[2-(2-octyl-1,3-dithiolan-2-yl)ethyl]imidazole;
1-[2-(2-nonyl-1,3-dithiolan-2-yl)ethyl]imidazole hydrochloride, m.p. 98°–101° C.;
1-[2-(2-decyl-1,3-dithiolan-2-yl)ethyl]imidazole;
1-[2-(2-cyclopentyl-1,3-dithiolan-2-yl)ethyl]imidazole;
1-[2-(2-(4-cyclopentylbutyl)-1,3-dithiolan-2-yl)ethyl]imidazole;

1-[2-(2-undecyl-1,3-dithiolan-2-yl)ethyl]imidazole;
1-[2-(2-cyclohexyl-1,3-dithiolan-2-yl)ethyl]imidazole;
1-[2-(2-dodecyl-1,3-dithiolan-2-yl)ethyl]imidazole;
1-[2-(2-(4-cyclohexylbutyl)-1,3-dithiolan-2-yl)ethyl]imidazole;
1-[2-(2-methyl-4-methyl-1,3-dithiolan-2-yl)ethyl]imidazole;
1-[2-(2-ethyl-4-methyl-1,3-dithiolan-2-yl)ethyl]imidazole;
1-[2-(2-propyl-4-methyl-1,3-dithiolan-2-yl)ethyl]imidazole;
1-[2-(2-t-butyl-4-methyl-1,3-dithiolan-2-yl)ethyl]imidazole;
1-[2-(2-pentyl-4-methyl-1,3-dithiolan-2-yl)ethyl]imidazole;
1-[2-(2-heptyl-4-methyl-1,3-dithiolan-2-yl)ethyl]imidazole;
1-[2-(2-nonyl-4-methyl-1,3-dithiolan-2-yl)ethyl]imidazole;
1-[2-(2-dodecyl-4-methyl-1,3-dithiolan-2-yl)ethyl]imidazole;
1-[2-(2-methyl-4-ethyl-1,3-dithiolan-2-yl)ethyl]imidazole;
1-[2-(2-cyclopentyl-4-ethyl-1,3-dithiolan-2-yl)ethyl]imidazole;
1-[2-(2-n-butyl-4-ethyl-1,3-dithiolan-2-yl)ethyl]imidazole;
1-[2-(2-hexyl-4-ethyl-1,3-dithiolan-2-yl)ethyl]imidazole;
1-[2-(2-octyl-4-ethyl-1,3-dithiolan-2-yl)ethyl]imidazole;
1-[2-(2-cyclohexyl-4-ethyl-1,3-dithiolan-2-yl)ethyl]imidazole;
1-[2-(2-decyl-4-ethyl-1,3-dithiolan-2-yl)ethyl]imidazole;
1-[2-(2-dodecyl-4-ethyl-1,3-dithiolan-2-yl)ethyl]imidazole;
1-[2-(2-methyl-4-n-butyl-1,3-dithiolan-2-yl)ethyl]imidazole;
1-[2-(2-ethyl-4-n-butyl-1,3-dithiolan-2-yl)ethyl]imidazole;
1-[2-(2-n-butyl-4-n-butyl-1,3-dithiolan-2-yl)ethyl]imidazole;
1-[2-(2-hexyl-4-n-butyl-1,3-dithiolan-2-yl)ethyl]imidazole;
1-[2-(2-nonyl-4-n-butyl-1,3-dithiolan-2-yl)ethyl]imidazole;
1-[2-(3-methyl-1,3-dithiolan-2-yl)propyl]imidazole;
1-[3-(2-ethyl-1,3-dithiolan-2-yl)propyl]imidazole;
1-[3-(2-propyl-1,3-dithiolan-2-yl)propyl]imidazole;
1-[3-(2-cyclopentyl-1,3-dithiolan-2-yl)propyl]imidazole;
1-[3-(2-t-butyl-1,3-dithiolan-2-yl)propyl]imidazole;
1-[3-(2-pentyl-1,3-dithiolan-2-yl)propyl]imidazole;
1-[3-(2-(4-cyclopentylbutyl)-1,3-dithiolan-2-yl)propyl]imidazole;
1-[3-(2-hexyl-1,3-dithiolan-2-yl)propyl]imidazole;
1-[3-(2-cyclohexyl-1,3-dithiolan-2-yl)propyl]imidazole;
1-[3-(2-heptyl-1,3-dithiolan-2-yl)propyl]imidazole;
1-[3-(2-octyl-1,3-dithiolan-2-yl)propyl]imidazole;
1-[3-(2-nonyl-1,3-dithiolan-2-yl)propyl]imidazole;
1-[3-(2-decyl-1,3-dithiolan-2-yl)propyl]imidazole;
1-[3-(2-dodecyl-1,3-dithiolan-2-yl)propyl]imidazole;
1-[3-(2-(4-cyclohexylbutyl)-1,3-dithiolan-2-yl)propyl]imidazole;
1-[3-(2-methyl-4-ethyl-1,3-dithiolan-2-yl)propyl]imidazole;
1-[3-(2-ethyl-4-ethyl-1,3-dithiolan-2-yl)propyl]imidazole;
1-[3-(2-propyl-4-ethyl-1,3-dithiolan-2-yl)propyl]imidazole;
1-[3-(2-n-butyl-4-ethyl-1,3-dithiolan-2-yl)propyl]imidazole;
1-[3-(2-octyl-4-ethyl-1,3-dithiolan-2-yl)propyl]imidazole;
1-[3-(2-dodecyl-4-ethyl-1,3-dithiolan-2-yl)propyl]imidazole;
1-[3-(2-methyl-4-methyl-1,3-dithiolan-2-yl)propyl]imidazole;
1-[3-(2-ethyl-4-methyl-1,3-dithiolan-2-yl)propyl]imidazole;
1-[3-(2-n-butyl-4-methyl-1,3-dithiolan-2-yl)propyl]imidazole;
1-[3-(2-nonyl-4-methyl-1,3-dithiolan-2-yl)propyl]imidazole;
1-[3-(2-undecyl-4-methyl-1,3-dithiolan-2-yl)propyl]imidazole;
1-[3-(2-methyl-4-n-butyl-1,3-dithiolan-2-yl)propyl]imidazole;
1-[3-(2-ethyl-4-n-butyl-1,3-dithiolan-2-yl)propyl]imidazole;
1-[3-(2-pentyl-4-n-butyl-1,3-dithiolan-2-yl)propyl]imidazole;
1-[3-(2-octyl-4-n-butyl-1,3-dithiolan-2-yl)propyl]imidazole;
1-[3-(2-dodecyl-4-n-butyl-1,3-di-thiolan-2-yl)propyl]imidazole.

EXAMPLE II

This example illustrates the preparation of Formula I(b) type compounds from Formula II type compounds.

A solution of 1-(octan-2-on-1-yl)imidazole (1.00 g) was mixed with 1,3-dithiopropane (2 ml) at room temperature 98% methanesulfonic acid (3 ml) was added in portions. The mixture stirred over night at room temperature. The resulting mixture was poured into excess aqueous potassium carbonate, extracted with ether and the extracts washed, dried with magnesium sulfate and the solvent evaporated. The resulting residue was chromatographed on silica gel to yield the free base which was precipitated from ether with ethereal hydrogen chloride. The resulting precipitate was filtered off and recrystallized from methanol/ethyl acetate to give 1-[2-hexyl-1,3-dithian-2-yl)methyl]imidazole hydrochloride.

Using the above conditions and steps but substituting the appropriate unsubstituted or substituted propane-1,3-dithiol and the appropriate ketone exemplified in Preparations 1, 2, 3 or 4 for 1-(octan-2-on-1-yl)imidazole, there may be prepared, for example, the following compounds:
1-[(2-methyl-1,3-dithian-2-yl)methyl]imidazole;
1-[(2-ethyl-1,3-dithian-2-yl)methyl]imidazole;
1-[(2-propyl-1,3-dithian-2-yl)methyl]imidazole;
1-[(2-cyclopentyl-1,3-dithian-2-yl)methyl]imidazole;
1-[(2-n-butyl-1,3-dithian-2-yl)methyl]imidazole;
1-[(2-pentyl-1,3-dithian-2-yl)methyl]imidazole;
1-[(2-hexyl-1,3-dithian-2-yl)methyl]imidazole;
1-[(2-cyclohexyl-1,3-dithian-2-yl)methyl]imidazole;
1-[(2-heptyl-1,3-dithian-2-yl)methyl]imidazole;
1-[(2-nonyl-1,3-dithian-2-yl)methyl]imidazole;
1-[(2-decyl-1,3-dithian-2-yl)methyl]imidazole;
1-[(2-undecyl-1,3-dithian-2-yl)methyl]imidazole;
1-[(2-dodecyl-1,3-dithian-2-yl)methyl]imidazole;
1-[(2-methyl-4-methyl-1,3-dithian-2-yl)methyl]imidazole;
1-[(2-ethyl-4-methyl-1,3-dithian-2-yl)methyl]imidazole;
1-[(2-propyl-4-methyl-1,3-dithian-2-yl)-methyl]imidazole;

1-[(2-n-butyl-4-methyl-1,3-dithian-2-yl)-methyl]imidazole;
1-[(2-pentyl-4-methyl-1,3-dithian-2-yl)methyl]imidazole;
1-[(2-hexyl-4-methyl-1,3-dithian-2-yl)methyl]imidazole;
1-[(2-heptyl-4-methyl-1,3-dithian-2-yl)methyl]imidazole;
1-[(2-octyl-4-methyl-1,3-dithian-2-yl)methyl]imidazole;
1-[(2-nonyl-4-methyl-1,3-dithian-2-yl)methyl]imidazole;
1-[(2-decyl-4-methyl-1,3-dithian-2-yl)methyl]imidazole;
1-[(2-dodecyl-4-methyl-1,3-dithian-2-yl)methyl]imidazole;
1-[(2-methyl-4-ethyl-1,3-dithian-2-yl)methyl]imidazole;
1-[(2-ethyl-4-ethyl-1,3-dithian-2-yl)methyl]imidazole;
1-[(2-propyl-4-ethyl-1,3-dithian-2-yl)methyl]imidazole;
1-[(2-pentyl-4-ethyl-1,3-dithiolan-2-yl)methyl]imidazole;
1-[(2-nonyl-4-ethyl-1,3-dithian-2-yl)methyl]imidazole;
1-[(2-undecyl-4-ethyl-1,3-dithian-2-yl)-methyl]imidazole;
1-[(2-methyl-4-n-butyl-1,3-dithian-2-yl)methyl]imidazole;
1-[(2-ethyl-4-n-butyl-1,3-dithian-2-yl)methyl]imidazole;
1-[(2-t-butyl-4-n-butyl-1,3-dithian-2-yl)methyl]imidazole;
1-[(2-hexyl-4-n-butyl-1,3-dithian-2-yl)methyl]imidazole;
1-[(2-octyl-4-n-butyl-1,3-dithian-2-yl)methyl]imidazole;
1-[(2-dodecyl-4-n-butyl-1,3-dithian-2-yl)methyl]imidazole;
1-[(2-methyl-1,3-dithian-2-yl)methyl]imidazole;
1-[(2-ethyl-1,3-dithian-2-yl)methyl]imidazole;
1-[(2-propyl-1,3-dithian-2-yl)methyl]imidazole;
1-[(2-n-butyl-1,3-dithian-2-yl)methyl]imidazole;
1-[(2-t-butyl-1,3-dithian-2-yl)methyl]imidazole;
1-[(2-nonyl-1,3-dithian-2-yl)methyl]imidazole;
1-[(2-dodecyl-1,3-dithian-2-yl)methyl]imidazole;
1-[(2-methyl-4-ethyl-1,3-dithian-2-yl)methyl]imidazole;
1-[(2-ethyl-4-ethyl-1,3-dithian-2-yl)methyl]imidazole;
1-[(2-n-butyl-4-ethyl-1,3-dithian-2-yl)methyl]imidazole;
1-[(2-octyl-4-ethyl-1,3-dithian-2-yl)methyl]imidazole;
1-[(2-dodecyl-4-ethyl-1,3-dithian-2-yl)methyl]imidazole;
1-[(2-methyl-4-methyl-1,3-dithian-2-yl)methyl]imidazole;
1-[(2-ethyl-4-methyl-1,3-dithian-2-yl)methyl]imidazole;
1-[(2-butyl-4-methyl-1,3-dithian-2-yl)methyl]imidazole;
1-[(2-heptyl-4-methyl-1,3-dithian-2-yl)methyl]imidazole;
1-[(2-decyl-4-methyl-1,3-dithian-2-yl)methyl]imidazole;
1-[(2-dodecyl-4-methyl-1,3-dithian-2-yl)methyl]imidazole;
1-[(2-methyl-4-n-butyl-1,3-dithian-2-yl)methyl]imidazole;
1-[(2-ethyl-4-n-butyl-1,3-dithian-2-yl)methyl]imidazole;
1-[(2-t-butyl-4-n-butyl-1,3-dithian-2-yl)methyl]imidazole;
1-[(2-hexyl-4-n-butyl-1,3-dithian-2-yl)methyl]imidazole;
1-[(2-nonyl-4-n-butyl-1,3-dithian-2-yl)methyl]imidazole;
1-[(2-dodecyl-4-n-butyl-1,3-dithian-2-yl)methyl]imidazole;
1-[2-(2-methyl-1,3-dithian-2-yl)ethyl]imidazole;
1-[2-(2-ethyl-1,3-dithian-2-yl)ethyl]imidazole;
1-[2-(2-propyl-1,3-dithian-2-yl)ethyl]imidazole;
1-[2-(2-n-butyl-1,3-dithian-2-yl)ethyl]imidazole;
1-[2-(2-pentyl-1,3-dithian-2-yl)ethyl]imidazole;
1-[2-(2-hexyl-1,3-dithian-2-yl)ethyl]imidazole;
1-[2-(2-heptyl-1,3-dithian-2-yl)ethyl]imidazole;
1-[2-(2-octyl-1,3-dithian-2-yl)ethyl]imidazole;
1-[2-(2-nonyl-1,3-dithian-2-yl)ethyl]imidazole;
1-[2-(2-decyl-1,3-dithian-2-yl)ethyl]imidazole;
1-[2-(2-undecyl-1,3-dithian-2-yl)ethyl]imidazole;
1-[2-(2-dodecyl-1,3-dithian-2-yl)ethyl]imidazole;
1-[2-(2-methyl-4-methyl-1,3-dithian-2-yl)ethyl]imidazole;
1-[2-(2-ethyl-4-methyl-1,3-dithian-2-yl)ethyl]imidazole;
1-[2-(2-propyl-4-methyl-1,3-dithian-2-yl)-ethyl]imidazole;
1-[2-(2-pentyl-4-methyl-1,3-dithian-2-yl)-ethyl]imidazole;
1-[2-(2-heptyl-4-methyl-1,3-dithian-2-yl)ethyl]imidazole;
1-[2-(2-nonyl-4-methyl-1,3-dithian-2-yl)-ethyl]imidazole;
1-[2-(2-dodecyl-4-methyl-1,3-dithian-2-yl)ethyl]imidazole;
1-[2-(2-methyl-4-ethyl-1,3-dithian-2-yl)ethyl]imidazole;
1-[2-(2-ethyl-4-ethyl-1,3-dithian-2-yl)-ethyl]imidazole;
1-[2-(2-n-butyl-4-ethyl-1,3-dithian-2-yl)ethyl]imidazole;
1-[2-(2-octyl-4-ethyl-1,3-dithian-2-yl)-ethyl]imidazole;
1-[2-(2-decyl-4-ethyl-1,3-dithian-2-yl)-ethyl]imidazole;
1-[2-(2-dodecyl-4-ethyl-1,3-dithian-2-yl)-ethyl]imidazole;
1-[2-(2-methyl-4-n-butyl-1,3-dithian-2-yl)ethyl]imidazole;
1-[2-(2-ethyl-4-n-butyl-1,3-dithian-2-yl)ethyl]imidazole;
1-[2-(2-n-butyl-4-n-butyl-1,3-dithian-2-yl)ethyl]imidazole;
1-[2-(2-hexyl-4-n-butyl-1,3-dithian-2-yl)ethyl]imidazole;
1-[2-(2-octyl-4-n-butyl-1,3-dithian-2-yl)ethyl]imidazole;
1-[2-(2-decyl-4-n-butyl-1,3-dithian-2-yl)ethyl]imidazole;
1-[2-(2-dodecyl-4-n-butyl-1,3-dithian-2-yl)ethyl]imidazole;
1-[3-(2-methyl-1,3-dithian-2-yl)propyl]imidazole;
1-[3-(2-ethyl-1,3-dithian-2-yl)propyl]imidazole;
1-[3-(2-propyl-1,3-dithian-2-yl)propyl]imidazole;
1-[3-(2-hexyl-1,3-dithian-2-yl)propyl]imidazole;
1-[3-(2-nonyl-1,3-dithian-2-yl)propyl]imidazole;
1-[3-(2-undecyl-1,3-dithian-2-yl)propyl]imidazole;
1-[3-(2-dodecyl-1,3-dithian-2-yl)propyl]imidazole;
1-[3-(2-methyl-4-methyl-1,3-dithian-2-yl)propyl]imidazole;
1-[3-(2-ethyl-4-methyl-1,3-dithian-2-yl)propyl]imidazole;
1-[3-(2-t-butyl-4-methyl-1,3-dithian-2-yl)propyl]imidazole;
1-[3-(2-heptyl-4-methyl-1,3-dithian-2-yl)propyl]imidazole;
1-[3-(2-nonyl-4-methyl-1,3-dithian-2-yl)propyl]imidazole;
1-[3-(2-decyl-4-methyl-1,3-dithian-2-yl)propyl]imidazole;
1-[3-(2-dodecyl-4-methyl-1,3-dithian-2-yl)propyl]imidazole;
1-[3-(2-ethyl-4-ethyl-1,3-dithian-2-yl)propyl]imidazole;
1-[3-(2-propyl-4-ethyl-1,3-dithian-2-yl)propyl]imidazole;
1-[3-(2-hexyl-4-ethyl-1,3-dithian-2-yl)propyl]imidazole;
1-[3-(2-octyl-4-ethyl-1,3-dithian-2-yl)propyl]imidazole;
1-[3-(2-nonyl-4-ethyl-1,3-dithian-2-yl)propyl]imidazole;
1-[3-(2-decyl-4-ethyl-1,3-dithian-2-yl)propyl]imidazole;
1-[3-(2-dodecyl-4-ethyl-1,3-dithian-2-yl)propyl]imidazole;
1-[3-(2-methyl-4-n-butyl-1,3-dithian-2-yl)propyl]imidazole;

1-[3-(2-ethyl-4-n-butyl-1,3-dithian-2-yl)propyl]imidazole;
1-[3-(2-n-butyl-4-n-butyl-1,3-dithian-2-yl)propyl]imidazole;
1-[3-(2-heptyl-4-n-butyl-1,3-dithian-2-yl)propyl]imidazole;
1-[3-(2-nonyl-4-n-butyl-1,3-dithian-2-yl)propyl]imidazole;
1-[3-(2-undecyl-4-n-butyl-1,3-dithian-2-yl)propyl]imidazole;
1-[3-(2-dodecyl-4-n-butyl-1,3-dithian-2-yl)propyl]imidazole;
1-[2-(2-methyl-5-methyl-1,3-dithian-2-yl)methyl]imidazole;
1-[2-(2-ethyl-5-methyl-1,3-dithian-2-yl)methyl]imidazole;
1-[2-(2-propyl-5-methyl-1,3-dithian-2-yl)methyl]imidazole;
1-[2-(2-n-butyl-5-methyl-1,3-dithian-2-yl)methyl]imidazole;
1-[2-(2-pentyl-5-methyl-1,3-dithian-2-yl)methyl]imidazole;
1-[2-(2-hexyl-5-methyl-1,3-dithian-2-yl)methyl]imidazole;
1-[2-(2-heptyl-5-methyl-1,3-dithian-2-yl)methyl]imidazole;
1-[2-(2-octyl-5-methyl-1,3-dithian-2-yl)methyl]imidazole;
1-[2-(2-decyl-5-methyl-1,3-dithian-2-yl)methyl]imidazole;
1-[(2-dodecyl-5-methyl-1,3-dithian-2-yl)methyl]imidazole;
1-[(2-methyl-5-ethyl-1,3-dithian-2-yl)-methyl]imidazole;
1-[(2-ethyl-5-ethyl-1,3-dithian-2-yl)methyl]imidazole;
1-[(2-t-butyl-5-ethyl-1,3-dithian-2-yl)methyl]imidazole;
1-[(2-octyl-5-ethyl-1,3-dithiolan-2-yl)methyl]imidazole;
1-[(2-decyl-5-ethyl-1,3-dithian-2-yl)methyl]imidazole;
1-[(2-dodecyl-5-ethyl-1,3-dithian-2-yl)methyl]imidazole;
1-[2-(2-methyl-5-ethyl-1,3-dithian-2-yl)ethyl]imidazole;
1-[2-(2-ethyl-5-ethyl-1,3-dithian-2-yl)ethyl]imidazole;
1-[2-(2-propyl-5-ethyl-1,3-dithian-2-yl)ethyl]imidazole;
1-[2-(2-hexyl-5-ethyl-1,3-dithian-2-yl)ethyl]imidazole;
1-[2-(2-nonyl-5-ethyl-1,3-dithian-2-yl)ethyl]imidazole;
1-[2-(2-dodecyl-5-ethyl-1,3-dithian-2-yl)ethyl]imidazole;
1-[2-(2-methyl-5-methyl-1,3-dithian-2-yl)ethyl]imidazole;
1-[2-(2-propyl-5-methyl-1,3-dithian-2-yl)ethyl]imidazole;
1-[2-(2-hexyl-5-methyl-1,3-dithian-2-yl)ethyl]imidazole;
1-[2-(2-nonyl-5-methyl-1,3-dithian-2-yl)ethyl]imidazole;
1-[2-(2-dodecyl-5-methyl-1,3-dithian-2-yl)ethyl]imidazole;
1-[3-(2-methyl-5-ethyl-1,3-dithian-2-yl)propyl]imidazole;
1-[3-(2-ethyl-5-ethyl-1,3-dithian-2-yl)propyl]imidazole;
1-[3-(2-n-butyl-5-ethyl-1,3-dithian-2-yl)propyl]imidazole;
1-[3-(2-hexyl-5-ethyl-1,3-dithian-2-yl)propyl]imidazole;
1-[3-(2-octyl-5-ethyl-1,3-dithian-2-yl)propyl]imidazole;
1-[3-(2-decyl-5-ethyl-1,3-dithian-2-yl)propyl]imidazole;
1-[3-(2-dodecyl-5-ethyl-1,3-dithian-2-yl)propyl]imidazole;
1-[3-(2-methyl-5-methyl-1,3-dithian-2-yl)propyl]imidazole;
1-[3-(2-ethyl-5-methyl-1,3-dithian-2-yl)propyl]imidazole;
1-[3-(2-propyl-5-methyl-1,3-dithian-2-yl)propyl]imidazole;
1-[3-(2-hexyl-5-methyl-1,3-dithian-2-yl)propyl]imidazole;
1-[3-(2-nonyl-5-methyl-1,3-dithian-2-yl)propyl]imidazole;
1-[3-(2-undecyl-5-methyl-1,3-dithian-2-yl)propyl]imidazole.

EXAMPLE III

Conversion of Free Bases to Salts

Ethereal hydrogen chloride was added dropwise to a stirred solution of 2.0 g. of 1-[2-propyl-1,3-dithiolan-2-yl)ethyl]imidazole in 30 ml. of anhydrous ether until precipitation was complete. The product was filtered off, washed with ether, air-dried and recrystallized from ethyl acetate/ethanol to yield 1-[(2-propyl-1,3-dithiolan-2-yl)-ethyl]imidazole hydrochloride —m.p. 118°–121° C.

In similar manner, all compounds of Formula (I) prepared in accordance with Examples I and II in base form can be converted to their pharmaceutically acceptable acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, or salicyclic acid, and the like.

EXAMPLE IV

Conversion of Salts to Free Bases

The compound 1-[2-(2-ethyl-4-methyl-1,3-dithiolan-2-yl)methyl]imidazole nitrate (2.0 g.) in 100 ml. of dichloromethane is shaken with excess dilute potassium carbonate solution until the salt was completely dissolved. The organic layer is then separated, washed twice with water, dried (MgSO$_4$) and evaporated to yield 1-[2-(2-ethyl-4-methyl-1,3-dithiolan-2-yl)methyl]imidazole as an oil.

In similar manner, the pharmaceutically acceptable acid addition salts of all compounds of Formula I as represented in Examples I and II can be converted to their corresponding compounds in base form.

EXAMPLE V

Conversion of One Salt to Another Salt

A solution of 1-[(2-octyl-1,3-dithiolan-2-yl)methyl]imidazole acetate in dry diethyl ether was treated dropwise with ethereal hydrogen chloride until precipitation was complete. The product was filtered off, washed with ether, dried in air and recrystallized from methanol/ethyl acetate to give the hydrochloride salt, m.p. 136°–138° C.

Similarly, proceeding as above, suitable pharmaceutically acceptable acid addition salts of compounds of Formula I can be converted to different suitable pharmaceutically acceptable acid addition salts.

EXAMPLE VI

The following illustrates formulations for vaginal administration in contraceptive uses of Formula I compounds such as the hydrochloride salt of 1-[(2-octyl-1,3-dithiolan-2-yl)methyl]imidazole.

(A) WATER SOLUBLE VAGINAL CREAM

| Ingredients | % w/w |
| --- | --- |
| Active ingredient | 1.0 |
| Cetostearyl alcohol | 12.0 |
| Polysorbate 60 | 2.0 |
| Sorbitan monostearate | 2.0 |
| Mineral oil | 2.0 |
| Propylene glycol | 4.0 |
| Benzyl alcohol | 1.0 |
| Butylated hydroxyanisole | 0.01 |
| Purified water qs ad | 100.0 |

All ingredients except the active ingredient, water, and 10% of the Polysorbate 60 are mixed and heated to 70°–80° C. 85% of the required water is separately heated to 70°–80° C. The remaining Polysorbate 60 and 10% of the water are dissolved together at 50°–60°, and the active ingredient dissolved therein.

The heated water is then added to the heated emulsifying ingredients using a homomixer at medium speed, with a final increase to high speed for 1 minute after mixing is complete. The homomixer is removed and mixing continued gently until the mixture congeals and cools to room temperature; whereupon the active ingredient, previously dissolved as described above, is added, and gentle mixing continued for 20–30 minutes. The remaining 5% of water is then used to rinse the vessels containing the premixed active ingredient and the rinse added to the total mixture. Mixing is continued and further water added if necesary.

For each application approximately 1 gm of the cream is administered vaginally to a fertile human female with a suitable syringe.

(B) VAGINAL JELLY

| Ingredients | % w/w |
| --- | --- |
| Active ingredient | 1.00 |
| Tragacanth | 3.00 |
| Acacia | 0.53 |
| Glycerin | 5.00 |
| Boric acid | 3.00 |
| Ricinoleic acid | 0.75 |
| p-hydroxybenzoic acid, propyl ester | 0.05 |
| Purified water qs ad | 100.0 |

The tragacanth and acacia are intermixed thoroughly with the glycerin; ricinoleic acid and active ingredient are then added to the mixture. The p-hydroxybenzoate and boric acid are dissolved in water (with heating if necessary), and the solution is added to the prior mixture, with stirring and warming to dissolve. The mixture becomes gelatinous upon cooling.

For each application approximately 1 gram of the gel is vaginally administered to a fertile human female with a suitable syringe.

(C) VAGINAL SUPPOSITORY

| Ingredients | % w/w |
| --- | --- |
| Active ingredient | 1.0 |
| Polyethylene glycol 4000 | 20.0 |
| Butylated hydroxyanisole | 0.01 |
| Polyethylene glycol 1000 qs ad | 100.0 |

The polyethylene glycol solids are mixed and heated to 70°–80° C., and the BHA dissolved in the mixture. After cooling to 45° C., the active ingredient is suspended in the above mixture by stirring. The suspension is poured into molds which are of sufficient size to form suppositories of about 3 gm each, and cooled.

(D) EFFERVESCENT VAGINAL TABLETS

| Ingredients | % w/w |
| --- | --- |
| Active ingredient | 1.0 |
| Anhydrous citric acid | 35.0 |
| Sodium bicarbonate | 15.0 |
| Polyethylene glycol 6000 | 20.0 |
| Lactose qs ad | 100.0 |

The above ingredients are combined and granulated using methanol as the solvent. The formulation is then dried and formed into tablets containing 20 mg of active compound with an appropriate tableting medicine.

(E) VAGINAL SPRAY-FOAM

| Ingredients | % w/w |
| --- | --- |
| Active ingredient | 2.0 |
| Emulsion base | 90.0 |
| Propellant 12/114 (40:60) | 8.0 |

The emulsion base is made up according to the following % w/w composition:

| | |
| --- | --- |
| myristic acid | 1.33 |
| stearic acid | 5.33 |
| cetyl alcohol | 0.50 |
| lanolin | 0.20 |
| isopropyl myristate | 1.33 |
| triethanolamine | 3.33 |
| glycerin | 4.70 |
| polyvinylpyrrolidine | 0.34 |
| purified water | 82.93 |

The ingredients of the emulsion base, except for the water, are mixed in a stainless steel container kept at 70°–80° C. 80% of the water to be used is also heated to 70°–80° C. and mixed during heating with a homomixer at moderate speed. After complete addition, the speed of mixing is increased for several minutes. The mixture is then cooled to room temperature and a solution containing the active ingredient in the remaining 20% water is added with continuous mixing. The preparation is placed in an appropriate spray can, topped with the propellant mixture, and sealed.

For each application approximately 0.5 gm of the foam are vaginally administered.

(F) VAGINAL SOLUBLE WAFFLE

| Ingredients | % w/w |
| --- | --- |
| Active ingredient | 1.0 |
| Starch | 10.0 |
| Water soluble lanolin qs ad | 100.0 |

The above ingredients are thoroughly mixed and pressed into 0.8 gm waffles with a suitable press.

EXAMPLE VII

The following pharmaceutical composition is representative of those which may be used for oral administration to a male mammal for contraceptive use or for orally treating microbial infections or for the treatment of convulsions.

| Ingredients | Parts by Weight |
|---|---|
| Active ingredient | 200 |
| Magnesium stearate | 3 |
| Starch | 30 |
| Lactose | 116 |
| Polyvinylpyrrolidone | 3 |

The above ingredients are combined and granulated using methanol as the solvent. The formulation is then dried and formed into tablets containing 200 milligrams of active compound with an appropriate tableting machine.

EXAMPLE VIII

The following illustrates the preparation of representative pharmaceutical formulations which may be used for controlling fungi, bacteria and protozoa utilizing an active compound such as the hydrochloride salt of 1-[(2-heptyl-1,3-dithiolan-2-yl)ethyl]imidazole.

TOPICAL FORMULATION

| A. | Ingredients | grams |
|---|---|---|
| | Active compound | 0.2-2 |
| | Span 60 | 2.0 |
| | Tween 60 | 2.0 |
| | Mineral oil | 5.0 |
| | Petrolatum | 10.0 |
| | Methyl paraben | 0.15 |
| | Propyl paraben | 0.05 |
| | BHA (butylated hydroxy anisole) | 0.01 |
| | Water qs | 100.0 |

All of the above ingredients, except water, are combined and heated to 60° C. with stirring. A sufficient quantity of water at 60° C. is then added with vigorous stirring to provide 100 g. of the cream formulation which is then cooled to room temperature.

I.V. FORUMLATION

| Ingredients | % w/v |
|---|---|
| Active compound | 0.5 g |
| Propylene glycol | 20.0 g |
| Polyethylene glycol 400 | 20.0 g |
| Tween 80 | 1.0 g |
| 0.9 Saline solution qs | 100.0 ml |

The active compound is dissolved in propylene glycol, polyethylene glycol 400 and Tween 80. A sufficient quantity of 0.9% saline solution is then added with stirring to provide 100 ml of the I.V. solution which is filtered through a 0.2 micron membrane filter and packaged under sterile conditions.

What is claimed is:

1. A compound having the formula

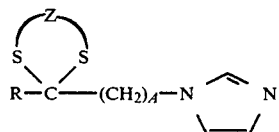

(I)

wherein

R is alkyl of 1 to 12 carbon atoms, cyclopentyl, cyclohexyl, cyclopentylloweralkyl or cyclohexylloweralkyl;

Z is ethylene or propylene, optionally substituted with a single substituent which is lower alkyl;

A is the integer 1, 2, or 3;

or a pharmaceutically acceptable acid addition salt thereof.

2. A compound according to claim 1 wherein R is alkyl of 1 to 12 carbon atoms.

3. A compound according to claim 2 wherein R is straight chain alkyl of 1 to 12 carbon atoms and Z is ethylene or ethylene optionally substituted with a single substituent which is lower alkyl.

4. A compound of claim 3 wherein R is 4 to 10 carbon atoms and A is 1 or 2.

5. A compound according to claim 4 which is 1-[2-(2-pentyl-1,3-dithiolan-2-yl)ethyl]imidazole or a pharmaceutically acceptable acid addition salt thereof.

6. A compound according to claim 4 which is 1-[2-(2-heptyl-1,3-dithiolan-2-yl)ethyl]imidazole or a pharmaceutically acceptable acid addition salt thereof.

7. A compound according to claim 4 which is 1-[2-(2-nonyl-1,3-dithiolan-2-yl)ethyl]imidazole or a pharmaceutically acceptable acid addition salt thereof.

8. A compound according to claim 4 which is 1-[(2-hexyl-1,3-dithiolan-2-yl)methyl]imidazole or a pharmaceutically acceptable acid addition salt thereof.

9. A compound according to claim 4 which is 1-[(2-n-butyl-1,3-dithiolan-2-yl)methyl]imidazole or a pharmaceutically acceptable acid addition salt thereof.

10. A compound according to claim 4 which is 1[(2-octyl-1,3-dithiolan-2-yl)methyl]imidazole or a pharmaceutically acceptable acid addition salt thereof.

11. A compound according to claim 4 which is 1-[(2-decyl-1,3-dithiolan-2-yl)methyl]imidazole or a pharmaceutically acceptable acid addition salt thereof.

12. A compound according to claim 1 wherein R is cyclopentyl, cyclohexyl, cyclopentylloweralkyl or cyclohexylloweralkyl and A is 1 or 2.

13. A compound according to claim 4 which is 1-[(2-cyclohexyl-1,3-dithiolan-2-yl)methyl]imidazole or a pharmaceutically acceptable acid addition salt thereof.

14. A spermicidal composition useful for effecting contraception in a male or female mammal which comprises a suitable excipient and an effective amount of a compound of the formula

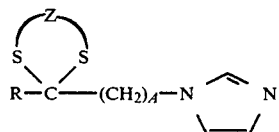

(I)

wherein

R is alkyl of 1 to 12 carbon atoms, cyclopentyl, cyclohexyl, cyclopentylloweralkyl or cyclohexylloweralkyl;

Z is ethylene or propylene, optionally substituted with a single substituent which is lower alkyl;

A is the integer 1, 2, or 3;

or a pharmaceutically acceptable acid addition salt thereof.

15. The composition of claim 14 for intravaginal administration wherein a compound of Formula I is present in an amount between 0.1 and 10 weight percent of the composition.

16. The composition of claim 14 for oral or parenteral administration to a male mammal wherein a compound of Formula I is present in an amount between 0.1 and 90 weight percent of the composition.

17. A method for effecting contraception in a male or female mammal by rendering spermatozoa ineffective, which method comprises administering to a subject an effective amount of at least one compound of the formula

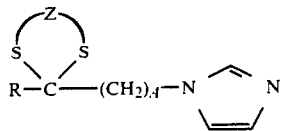

wherein
- R is alkyl of 1 to 12 carbon atoms, cyclopentyl, cyclohexyl, cyclopentylloweralkyl or cyclohexylloweralkyl;
- Z is ethylene or propylene, optionally substituted with a single substituent which is lower alkyl;
- A is the integer 1, 2, or 3;

or a pharmaceutically acceptable acid addition salt thereof.

18. The method of claim 17 wherein a compound of Formula I is administered intravaginally to a female mammal.

19. The method of claim 17 wherein a compound of Formula I is administered orally or parenterally to a male mammal.

* * * * *